LINDEN TREE
Filed Nov. 5, 1970 2 Sheets-Sheet 1
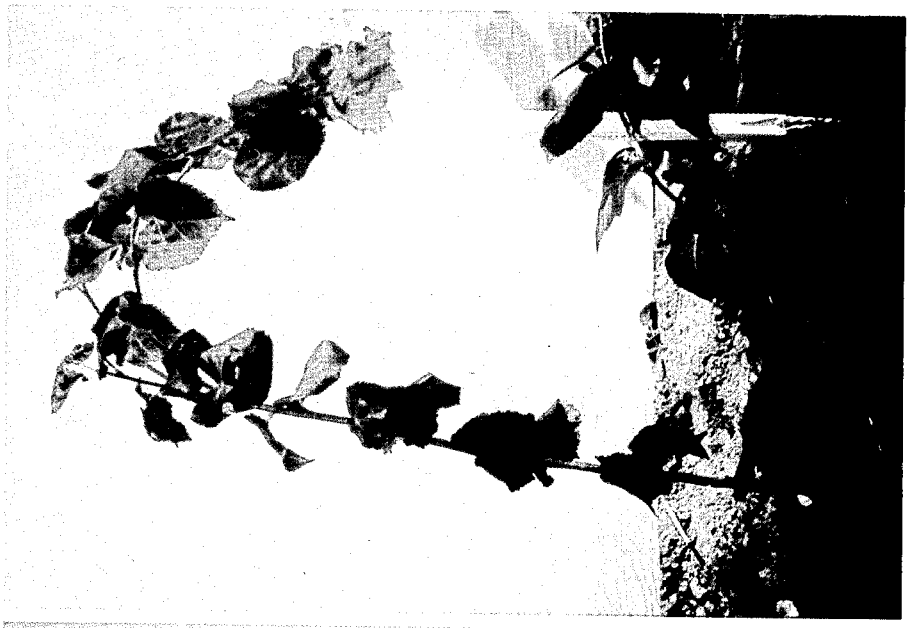
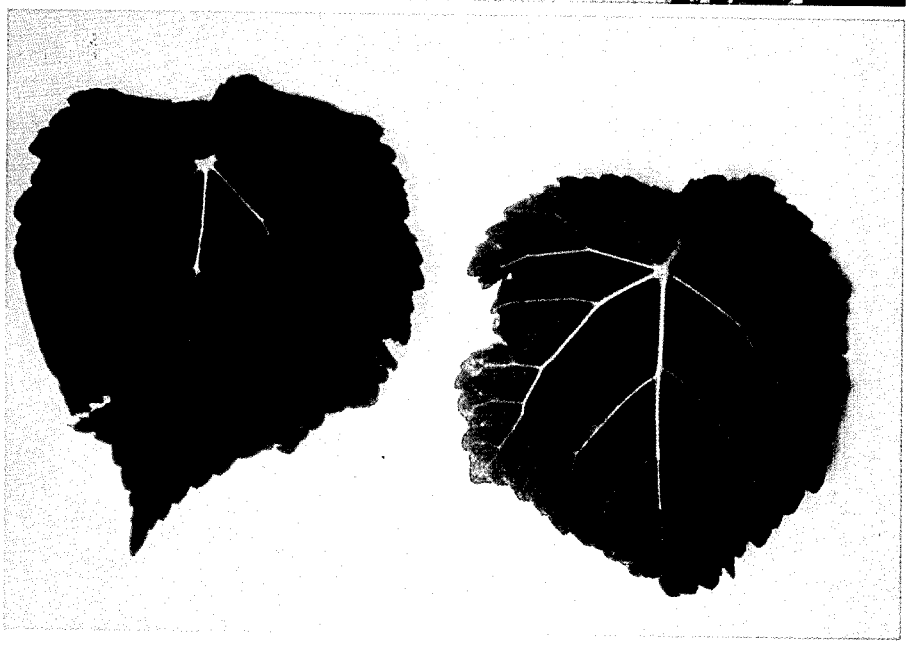
Inventor.
J. H. McIntyre
By: Robb & Robb
Attorneys.

LINDEN TREE
Filed Nov. 5, 1970 2 Sheets-Sheet 2
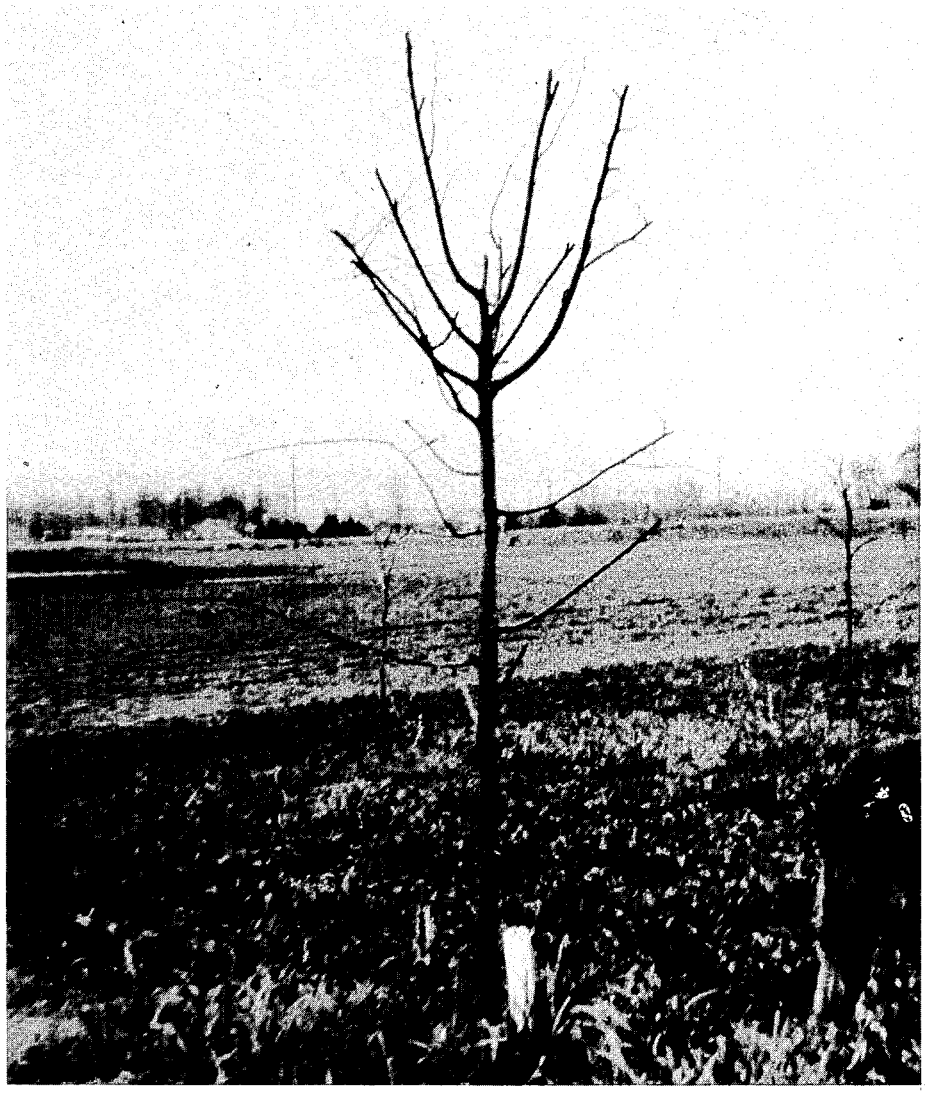

United States Patent Office

Plant Pat. 3,259
Patented Aug. 22, 1972

3,259

LINDEN TREE

John H. McIntyre, Gresham, Oreg., assignor to The W. E. McGill Trust, doing business as A. McGill and Son, Fairview, Oreg.

Filed Nov. 5, 1970, Ser. No. 87,364
Int. Cl. A01h *5/00*
U.S. Cl. Plt.—51 1 Claim

The present invention relates to a new and distinct variety of linden tree which was discovered by me in a field of linden seedlings of the species botanically known as *Tilia cordata* being grown under my direction and supervision on the nursery property of my assignee located at Fairview, Oreg.

At the time of my discovery aforesaid the field of seedlings had been planted and were being grown for understock, and my attention was attracted to one particular seedling which was larger in size than the average of the seedlings in the field, and because it also bore darker colored and somewhat heavier leaves. I promptly preserved this particular seedling and kept it under close observation. Continued observations and tests of the new seedling, as well as progeny thereof derived from buddings made by me in the nursery aforementioned, have conclusively confirmed and establishded that the seedling is unique and definitely distinguished from all other varieties of the species *Tilia cordata* of which I am aware, as evidenced by the following combination of characteristics which are outstanding in the new seedling:

(1) A strong growing habit;
(2) A larger leaf size than is normal for the species *Tilis cordata;*
(3) A heavier than normal leaf thickness; and
(4) A distinctive, attractive and darker than normal green leaf color.

The accompanying drawings show a typical young tree specimen about one year old and typical foliage specimens on a somewhat larger scale than in the view of the tree specimen, all as depicted in color as nearly true as it is reasonably possible to make the same in an illustration of this type. The drawings also show in black and white a typical three-year-old bare tree speciment which has been cut back in taking scion wood therefrom, but illustrating its sturdy growth habit and typical branching habit.

The following is a detailed description of my new variety of linden tree, with color terminology in accordance with the Exotica Horticultural Color Guide, published by Roehrs Company, of Rutherford, N.J.:

Parentage: A *Tilia cordata* seedling of unknown parentage.

Propagation: Holds its distinguishing characteristics through succeeding propagations by budding.

Locality where grown and observed: Fairview, Oreg.

Tree: Vigorous grower (averages about one foot taller than normal for the species the first year and continuing faster growing in succeeding years when grown on the same root-stock and in the same fields); medium spreading; tall.

*Trunk.*—Smooth.

*Branches.*—Smooth; branches extend radially from trunk in all directions instead of being largely in a single plane as is common for most varieties of the species. Color—Chocolate, Color No. 7. Lenticels—average number for the species.

Foliage:

*Leaves.*—Thick; tough; somewhat dull and rough. Quantity—profuse. Size—larger than average for th species. Length—average from 12.5 cm. to 14.5 cm. Width—average from 9.0 cm. to 11.0 cm. Shape—Apex ranges from near acute to obtuse, and base ranges from cordate to sagittate. Color—upper surface—Ivy Green, Color No. 70+. Under surface—Olive Green, Color No. 84. Margin—mixture of dentate and crenate. Petiole—medium length with respect to the species; ranges from about 2½ cm. long. Glands—none.

Flower buds: None observed.

I claim:

1. A new and distinct variety of linden tree of the species botanically known as *Tilia cordata,* substantially as herein shown and described, characterized particularly as to novelty by the unique combination of a strong growing habit, a larger leaf size than is normal for the species *Tilia cordata,* a heavier than normal leaf thickness, and a distinctive, attractive and darker than normal green leaf color.

References Cited

UNITED STATES PATENTS

P.P. 2,086 9/1961 Flemer ---------- Plants 51

ROBERT E. BAGWILL, Primary Examiner